United States Patent [19]

Evans et al.

[11] Patent Number: 5,736,637
[45] Date of Patent: Apr. 7, 1998

[54] DOWNHOLE MULTIPHASE FLOW SENSOR

[75] Inventors: John T. Evans; Stanislav Forgang; Gregory B. Itskovich, all of Houston, Tex.

[73] Assignee: Western Atlas International, Inc., Houston, Tex.

[21] Appl. No.: 647,631

[22] Filed: May 15, 1996

[51] Int. Cl.$^6$ ............................................. E21B 49/00
[52] U.S. Cl. ........................... 73/152.31; 73/152.18; 73/152.19; 73/152.21; 73/152.29
[58] Field of Search ....................... 73/152.18, 152.19, 73/152.21, 152.29, 152.31, 152.55, 861.14, 861.08

[56] References Cited

U.S. PATENT DOCUMENTS

| | | | |
|---|---|---|---|
| 3,279,249 | 10/1966 | Tocanne | 73/152.31 |
| 3,514,996 | 6/1970 | Coustau | 73/152.31 |
| 3,721,121 | 3/1973 | Fierfort | 73/152.55 X |
| 4,441,362 | 4/1984 | Carlson | 73/152.31 |
| 4,480,484 | 11/1984 | Ueyama | 73/861.08 |
| 4,974,446 | 12/1990 | Vigneaux | 73/861.04 X |
| 5,132,903 | 7/1992 | Sinclair | 73/152.55 X |
| 5,239,862 | 8/1993 | Atkinson | 73/65.56 X |
| 5,251,479 | 10/1993 | Siegfried II et al. | 73/152.29 |
| 5,456,120 | 10/1995 | Simonian | 73/861.04 |
| 5,531,112 | 7/1996 | Young et al. | 73/152.02 |
| 5,596,150 | 1/1997 | Arndt et al. | 73/861.12 |

*Primary Examiner*—Elizabeth L. Dougherty
*Attorney, Agent, or Firm*—Alan J. Atkinson

[57] ABSTRACT

A system for evaluating multiphase flow of a fluid downhole in a borehole. Dielectric permittivity electrodes generate a capacitance output signal through the fluid, and conductivity electrodes generate a conductivity output signal through the fluid. The electrodes are powered with an AC generator operating at the same or different frequencies. The capacitance and conductivity output signals can be alternately generated by operating a controller, and such signals can be combined with a multiplexer engaged with the controller. The signal can be processed downhole or can be transmitted to a receiver positioned at the well surface for processing and interpretation of the multiphase data.

10 Claims, 2 Drawing Sheets

DOWNHOLE MULTIPHASE FLOW SENSOR

BACKGROUND OF THE INVENTION

The present invention relates to the downhole evaluation of formation fluids produced into a wellbore. More particularly, the present invention relates to a system that simultaneously combines conductivity and dielectric permittivity sensors in a single downhole module for real-time multiphase flow evaluation.

Fluids are produced from a borehole drilled into the formation rock. The fluids are tested to evaluate the presence of hydrocarbons, the flowrate, and the presence of multiphase fluids created by the combination of water and hydrocarbons. The resulting data provides information regarding the concentration of hydrocarbons in the formation. The data also provides information regarding the composition and location of hydrocarbons and suggests procedures for maximizing the completion and production of hydrocarbon reservoirs.

The composition of formation fluids can be identified by certain electrical characteristics. Hydrocarbon fluids have a low conductivity, while salt water fluids typically found in subsurface formations have a relatively high conductivity. Because of this fundamental difference in conductivity, downhole sensors measure the conductivity of the formation fluids. Relative conductivity is evaluated by measuring the amount of current transmitted through the formation fluid sample between two or more electrodes when a selected voltage is applied to source electrodes.

In addition to conductivity characteristics, hydrocarbon fluids have a different dielectric permittivity than salt water brines. Dielectric permittivity sensors are usually constructed as a capacitor and measure changes in the capacitor's dielectric. However, dielectric permittivity sensors cannot effectively operate in a conductive medium where the conductivity of the formation fluid exceeds 0.0001 Sim/m. This phenomenon occurs because the displacement currents between the capacitor plates become negligible when compared to galvanic currents in the formation fluid.

Sensors have also been used to evaluate multiphase flow in pipelines. In European Patent Application No. 0510774A2 to Den Boer et al, a plurality of capacitors were positioned vertically in a pipeline by placing a single electrode on one side of the fluid sample and a segmented electrode on the other side of the fluid. Higher placed electrode segments identified the fluid level in the pipeline, and lower placed electrode segments measured the impedance of the liquid. The watercut in the liquid-filled part of the pipeline was determined by calculating the dielectric constant of the fluid from the capacator impedance measurement. This watercut calculation was based on a theoretical relationship between the dielectric constant of an oil/water mixture and the ratio of water in the oil.

Although downhole sensors have been constructed to evaluate the dielectric properties of formation fluids, such sensors do not provide stable and accurate results when the fluids are electrically conductive. Measurement of dielectric permittivity and conductivity is complicated by the physical difficulty in measuring these parameters at low frequencies with the same electrodes. Accordingly, a need exists for an improved downhole sensor that can accurately and efficiently evaluate multiphase formation fluids.

SUMMARY OF THE INVENTION

The present invention provides an apparatus and method for evaluating multiphase flow of a fluid downhole in a borehole. The invention comprises a housing insertable in the borehole at a selected position, a flow space in the housing for permitting movement of the fluid through the flow space, first and second dielectric permittivity electrodes for producing a capacitance output signal, first and second conductivity electrodes for producing a conductivity output signal, an electric power source engaged with said electrodes, and a controller for receiving said capacitance output signal and said conductivity output signal.

In other embodiments of the invention, a multiplexer can be engaged with said controller, and the capacitance and conductivity output signals can be transmitted to a receiver at the well surface. The controller can selectively control the operation of the dielectric permittivity electrodes or conductivity electrodes, and can process the respective output signals downhole in the borehole.

The method of the invention is practiced by providing a housing at a desired downhole position, by flowing the fluid through a flow space within the housing, by generating a capacitance output signal from dielectric permittivity electrodes proximate to the fluid, by generating a conductivity output signal from conductivity electrodes in contact with the fluid, and by operating a controller to receive said capacitance output signal and said conductivity output signal.

DESCRIPTION OF THE PREFERRED EMBODIMENTS

Figure 1:
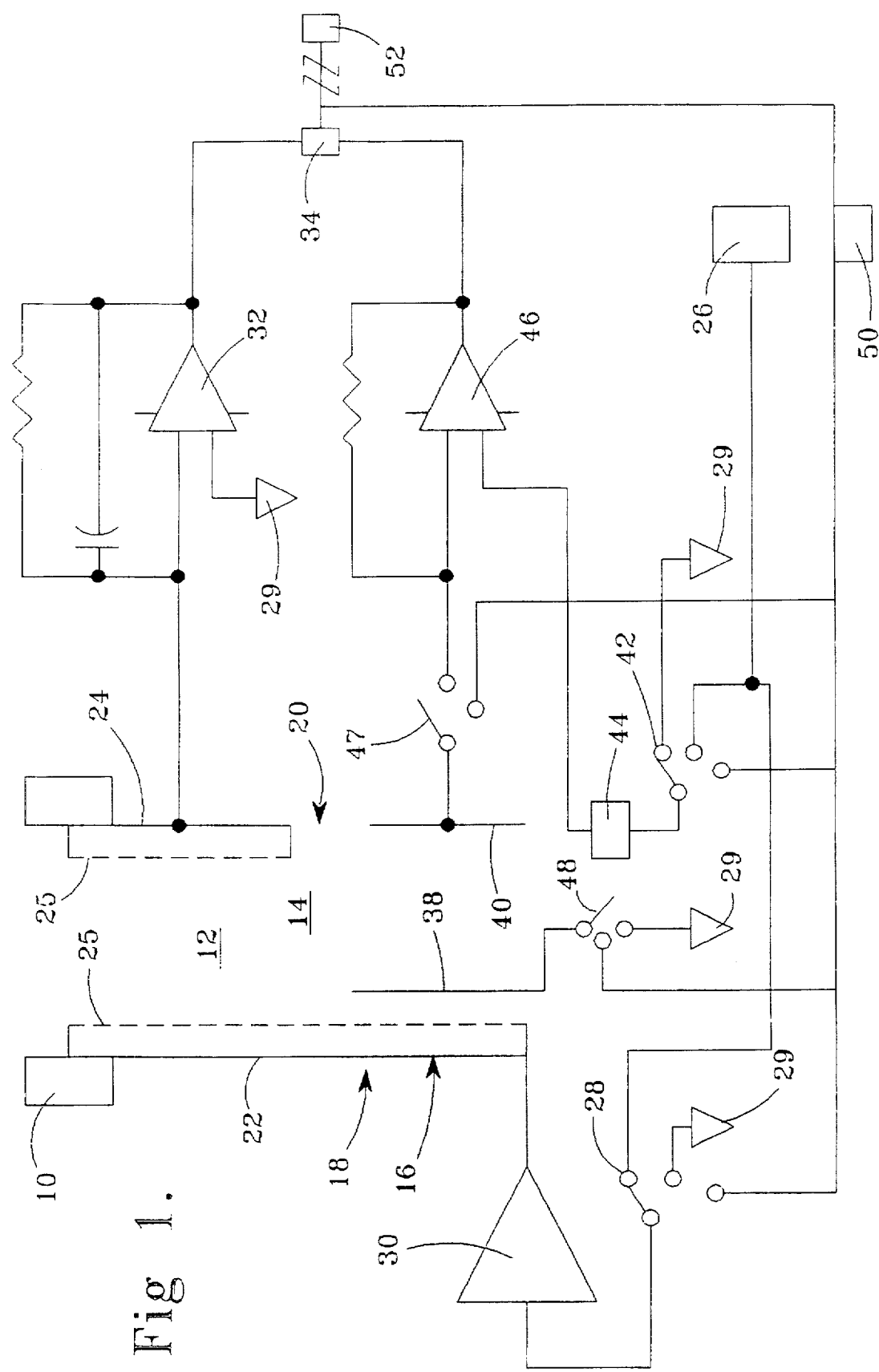
FIG. 1 illustrates a schematic diagram for one embodiment of the invention.

The present invention furnishes a downhole system that simultaneously generates conductivity and dielectric permittivity outputs from a single sensor or sensor array. Referring to FIG. 1, a schematic view for one embodiment of the invention is shown. Housing 10 can be positioned downhole within a vertical, inclined, or horizontal borehole section. Housing 10 encloses a space identified as fluid flow space 12, which is in fluid communication with the formation fluid 14 outside of housing 10. Fluid 14 selectively enters fluid flow space 12 through a port or valve device (not shown).

Sensor 16 is attached to housing 10 and is engaged with fluid flow space 12 to measure the conductivity and dielectric permittivity of fluid 14. Sensor 16 includes modules 18 and 20 on opposite sides of fluid flow space 12. Electrode 22 is positioned on the surface of module 18, and correlative electrode 24 is positioned opposite electrode 22 on the surface of module 20. Electrodes 22 and 24 are used for dielectric permittivity measurements, and are galvanically insulated from fluid 14 by a thin layer of non-conductive material 25.

Electrode 22 is charged with alternating electric current from AC generator 26, and can be interrupted with electronic switch 28 grounded to sensor common 29. In one embodiment of the invention illustrated in FIG. 1, the AC electric current is generated at 66.5 kHz. Other frequencies can be used alone or in combination to generate different signals. Capacitance source driver 30 enhances the signal provided to electrode 22. The output of dielectric permittivity is enhanced with amplifier 32 and is multiplexed into a single A/D converter 34.

In an alternative embodiment of the invention, electrode 22 can be connected to AC generator 26 by employing an electronic switch and driver circuit (not shown). The electronic switch can be connected to AC generator 26 when dielectric permittivity measurements are made, the driver circuit can be an inverting buffer formed with an op amp and a buffer IC. Other circuits and combinations of components can be constructed without departing from the scope of the invention.

Conductivity measurements are performed by transmitting current through fluid 14 between electrodes 38 and 40. Electrodes 38 and 40 are preferably constructed with a low polarization metal such as gold or platinum and are in direct contact with fluid 14. Electrode 38 is attached to sensor module 18, and electrode 40 is attached to module 20. Electrode 40 is powered with AC generator 26 through electronic switch 42, attenuator 44, non-inverting amplifier 46, and electronic switch 47. Electronic switch 47 selectively interrupts the circuit between electrode 40 and amplifier 46. Electrode 38 is engaged with sensor common 29 to complete the conductivity circuit, and switch 48 can be positioned between electrode 38 and sensor common 29 as described below.

Controller 50 can be attached to housing 10 downhole in a borehole or can be located at the well surface. Controller 50 can perform different control and computation functions. In the embodiment illustrated in FIG. 1, controller 50 is illustrated as being engaged with electronic switch 42 for selectively transmitting power from AC generator 26 to electrode 40, with electronic switch 47 for selectively interrupting the circuit between electrode 40 and amplifier 46, with switch 48 for selectively interrupting the circuit between electrode 38 and sensor common 29, and with switch 28 for selectively interrupting the circuit between AC generator 26 and electrode 22. In this configuration, controller 50 can selectively complete either the conductivity or dielectric permittivity circuits.

Controller 50 also receives the capacitance output signal and the conductivity output signal, and controls the operation of A/D converter or multiplexer 34 to receive such signals. Controller 50 permits the capacitance and conductivity signals to be multiplexed quickly enough to reduce possible motion errors of heterogeneous fluid 14 through flow space 12. Controller 50 controls electronic switches 28, 48, 42, 47 and multiplexer 34 to efficiently acquire data for a particular task. If the task requires conductivity and capacitance signals, the following sequence can be performed with controller 50:

1. Switch 28 can be set for the capacitance mode, and one or more capacitance channels from electrodes 22 and 24 can be sequentially multiplexed and digitized by multiplexer or A/D converter 34.

2. Switch 28 is reversed, and switches 42, 47 and 48 are operated to change sensor 16 to the conductivity mode. One or more auxiliary channels may be multiplexed and digitized while sensor transients are settling. Controller 50 commands multiplexer 34 to sequentially multiplex through and digitize the signals from one or more conductivity electrodes like 38 and 40.

3. Switches 28, 42, 47 and 48 are operated to move the system back to the capacitance mode, and one or more auxilliary channels are multiplexed and digitized while sensor transients are settling.

4. Controller 50 returns to step 1 and repeats sequence.

The invention uses a single sensor or multiple sensor arrays having modules to measure conductivity and dielectric permittivity of a downhole fluid. The invention provides a real time evaluation of multiphase flow, and operates the conductivity and dielectric permittivity sensing electrodes sequentially by using multiplexing principles for the inputs. By multiplexing the conductivity and dielectric permittivity imput signals, data can be collected virtually simultaneously as the downhole fluid flows through the defined flow space. The data is communicated in a form that facilitates processing and interpretation of the multiphase signal data detected with the system electrodes. The invention further permits the comparison of different data indicating dielectric permittivity and conductivity, thereby providing additional information previously unavailable in a single instrument package. The operation of generator 26 is preferably synchronized with controller 50 and with the multiplexing operations to facilitate the identification of signals within the system. All of these benefits significantly enhance the overall efficiency of the data acquisition.

The dielectric permittivity and conductivity sensors can incorporate ungrounded "floating" electronics to avoid galvanic contacts with housing 10 and other components in the system. Communication telemetry can be provided with a high-speed non-conductive coupler such as an optic or capacitance coupler.

Figure 2:
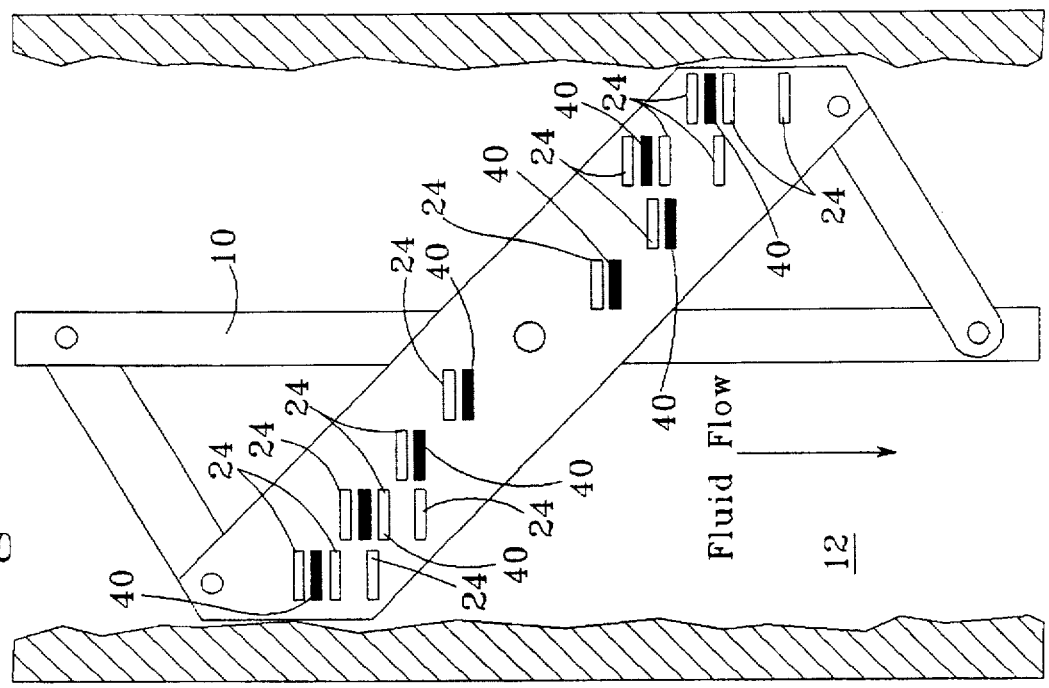
FIG. 2 illustrates an elevation view of a sensor having conductivity and dielectric permittivity electrodes.

FIG. 2 illustrates one embodiment of module 20 having an array of electrodes. Electrode 22 in module 18 cooperates with module 20 to measure dielectric permittivity, and electrodes 38 in module 18 cooperate with module 20 to measure conductivity. The orientation of electrodes 24 and electrodes 40 on the same module is illustrated by FIG. 2. Electrodes 18 and electrodes 38 can be linearly shaped and oriented to be perpendicular to the flow direction of formation fluid 14. Discontinuities in formation fluid 14 will be detected by different electrode pairs as the fluid flows through flow space 12, thereby providing information regarding the formation fluid flow rate and other data.

Figure 3:
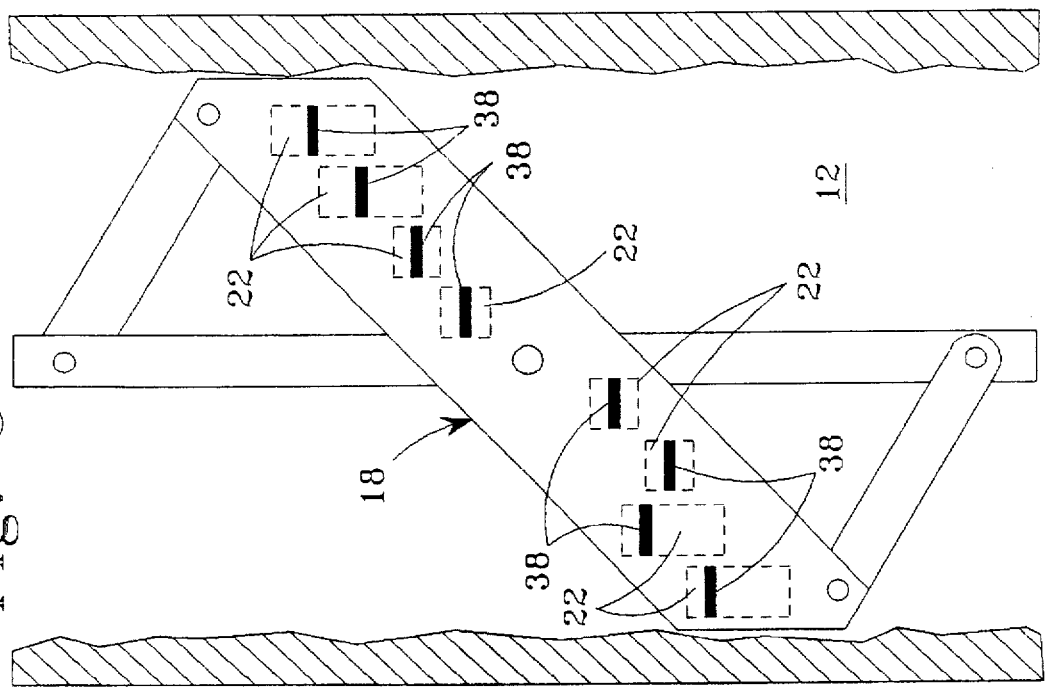
FIG. 3 illustrates a mirror image view of the sensor shown in FIG. 2.

FIG. 3 illustrates on embodiment of module 18 wherein an array of conductivity electrodes 38 and dielectric permittivity electrodes 22 are arranged to correspond with electrodes 40 and 24 in FIG. 2. FIG. 3 represents the mirror image of FIG. 2, and can be formed in different configurations to accomplish the function of the invention.

The invention is particularly suitable for logging tools, and is particularly useful in deviated or horizontal wellbores where the formation fluids are found in multiple phase conditions within the same wellbore. The invention can be temporarily run into the wellbore as a logging tool, or can be positioned downhole in a wellbore to evaluate the formation fluids over a long period of time.

Although the data processing and evaluation could be performed by the downhole controller, such functions could also be performed at the wellbore surface. Referring to FIG. 1, receiver 52 is positioned at the wellbore surface and is in communication with multiplexer 34 and controller 50. Receiver 52 receives the multiplexed signal and can include components for demodulating such signal and for evaluating the signal data. In one embodiment of the invention, receiver 52 can send command signals downhole to controller 50 for the purpose of monitoring or controlling various functions. Signal demodulation or evaluation can also be accomplished within controller 50, in which case processed signals can be communicated to receiver 52.

Although the invention has been described in terms of certain preferred embodiments, it will be apparent to those of ordinary skill in the art that modifications and improvements can be made to the inventive concepts herein without departing from the scope of the invention. The embodiments shown herein are merely illustrative of the inventive concepts and should not be interpreted as limiting the scope of the invention.

What is claimed is:

1. An apparatus for evaluating multiphase flow of a fluid downhole in a borehole, comprising:
   a housing insertable in the borehole at a desired downhole position;
   a flow space within said housing for permitting movement of the fluid through said flow space;
   an array of first and second dielectric permittivity electrodes in contact with the fluid in said flow space for producing a capacitance output signal;
   an array of first and second conductivity electrodes in contact with the fluid in said flow space for producing a conductivity output signal;
   an electric power source engaged with said dielectric permittivity electrodes and with said conductivity electrodes; and
   a controller for receiving said capacitance output signal and said conductivity output signal.

2. An apparatus for evaluating multiphase flow of a fluid downhole in a borehole, comprising:
   a housing insertable in the borehole at a desired downhole position;
   a flow space within said housing for permitting movement of the fluid through said flow space;
   a first dielectric permittivity electrode in contact with the fluid in said flow space;
   a second dielectric permittivity electrode in contact with the fluid and engaged with said first dielectric permittivity electrode for producing a capacitance output signal;
   a first conductivity electrode in contact with the fluid in said flow space; a second conductivity electrode engaged with said first conductivity electrode for producing a conductivity output signal;
   an electric power source engaged with said dielectric permittivity electrodes and with said conductivity electrodes, wherein said electric power source is capable of varying the frequency of the electric power transmitted to said electrodes; and
   a controller for receiving said capacitance output signal and said conductivity output signal.

3. An apparatus for generating an electric signal representating multphase flow of a fluid downhole in a borehole, comprising:
   a housing insertable in the borehole at a selected downhole position;
   a flow space within said housing for permitting movement of the fluid through said flow space;
   a first module having an insulated dielectric permittivity electrode and having a conductivity electrode in contact with the fluid in said flow space;
   a second module in contact with the fluid in said flow space, wherein said second module includes an insulated dielectric permittivity electrode engaged with said first module dielectric permittivity electrode for producing a capacitance output signal, and includes a conductivity electrode engaged with said first module conductivity electrode for producing a conductivity output signal;
   an electric power source engaged with said dielectric permittivity electrodes and with said conductivity electrodes; and
   a controller for receiving said capacitance output signal and said conductivity output signal.

4. An apparatus as recited in claim 3, further comprising a multiplexer engaged with said controller for receiving said capacitance output signal and for receiving said conductivity output signal.

5. An apparatus as recited in claim 3, further comprising a first switch between said generator and said first module dielectric permittivity electrode for selectively communicating electric power to said dielectric permittivity electrode.

6. An apparatus as recited in claim 5, further comprising a second switch between said generator and said first module conductivity electrode for selectively communicating electric power to said conductivity electrode.

7. An apparatus as recited in claim 6, further comprising a third switch between said generator and said second module conductivity electrode for selectively communicating electric power to said conductivity electrode.

8. An apparatus as recited in claim 7, wherein said controller selectively controls said first, second and third switches.

9. An apparatus as recited in claim 3, wherein said controller is positioned adjacent said housing downhole in the borehole.

10. An apparatus as recited in claim 9, further comprising a receiver attached to said controller for receiving a signal comprising said capacitance output signal and said conductivity output signal.

* * * * *